(12) United States Patent
Caldwell et al.

(10) Patent No.: US 6,945,932 B1
(45) Date of Patent: Sep. 20, 2005

(54) SURGICAL ACCESS DEVICE

(75) Inventors: Martin Caldwell, Dublin (IE); Christy Cummins, County Offaly (IE); Mike Muntner, County Dublin (IE)

(73) Assignee: Gaya Limited, Dublin (IE)

( * ) Notice: Subject to any disclaimer, the term of this patent is extended or adjusted under 35 U.S.C. 154(b) by 0 days.

(21) Appl. No.: 09/936,841

(22) PCT Filed: Mar. 20, 2000

(86) PCT No.: PCT/IE00/00033

§ 371 (c)(1),
(2), (4) Date: Mar. 1, 2002

(87) PCT Pub. No.: WO00/54676

PCT Pub. Date: Sep. 21, 2000

(30) Foreign Application Priority Data

Mar. 18, 1999 (IE) .................................... S990220

(51) Int. Cl.⁷ ............................................. A61B 19/00
(52) U.S. Cl. ........................... 600/208; 606/1; 606/213
(58) Field of Search ................... 606/1, 21.3; 128/897, 128/898, 850; 600/208, 235

(56) References Cited

U.S. PATENT DOCUMENTS

| 1,157,202 A | 10/1915 | Bates et al. |
| 3,347,227 A | 10/1967 | Harrower |
| 4,984,564 A | 1/1991 | Yuen |
| 5,159,921 A | 11/1992 | Hoover |
| 5,213,114 A | 5/1993 | Bailey, Jr. |
| 5,366,478 A | 11/1994 | Brinkerhoff et al. |
| 5,514,133 A | 5/1996 | Golub et al. |
| 5,522,791 A | 6/1996 | Leyva |
| 5,524,644 A | 6/1996 | Crook |
| 5,545,179 A | 8/1996 | Williamson, IV |
| 5,634,937 A | 6/1997 | Mollenauer et al. |
| 5,640,977 A | 6/1997 | Leahy et al. |
| 5,649,550 A | 7/1997 | Crook |
| 5,810,721 A | 9/1998 | Mueller et al. |
| 5,871,474 A | 2/1999 | Hermann et al. |
| 5,906,577 A | 5/1999 | Beane et al. |
| 6,033,426 A | 3/2000 | Kaji |
| 6,033,428 A | 3/2000 | Sardella |
| 6,077,288 A | 6/2000 | Shimomura et al. |
| 6,142,935 A | 11/2000 | Flom et al. |

(Continued)

FOREIGN PATENT DOCUMENTS

| WO | WO 95/07056 | 3/1995 |
| WO | WO 95/07056 A2 | 3/1995 |
| WO | WO 99/25268 | 5/1999 |
| WO | WO 00/32120 A1 | 6/2000 |
| WO | WO 00/35356 A1 | 6/2000 |
| WO | WO 01/08581 | 2/2001 |
| WO | WO 01/26559 A1 | 4/2001 |
| WO | WO 02/34108 A2 | 5/2002 |

*Primary Examiner*—Michael Thaler
(74) *Attorney, Agent, or Firm*—Nixon Peabody LLP; Tim L. Brackett, Jr.

(57) ABSTRACT

Surgical device (1) is for use in minimally invasive surgery using an inflated body cavity (2) accessible to a surgeon through an access port defined by a sleeve (4) passing through an incision in a patient's abdominal wall (3). The device is held in position by a distal ring (5) and a proximal ring (6). The device (1) is sealed by cuff valve (8), self sealing valve (18), spring valve (28) or snap open/snap shut valve (38).

16 Claims, 2 Drawing Sheets

U.S. PATENT DOCUMENTS

| | | |
|---|---|---|
| 6,149,642 A | 11/2000 | Gerhart et al. |
| 6,254,533 B1 | 7/2001 | Fadem et al. |
| 6,254,534 B1 | 7/2001 | Butler et al. |
| 6,276,661 B1 | 8/2001 | Laird |
| 6,382,211 B1 | 5/2002 | Crook |
| 6,440,063 B1 | 8/2002 | Beane et al. |
| 6,450,983 B1 | 9/2002 | Rambo |
| 2001/0037053 A1 | 11/2001 | Bonadio et al. |

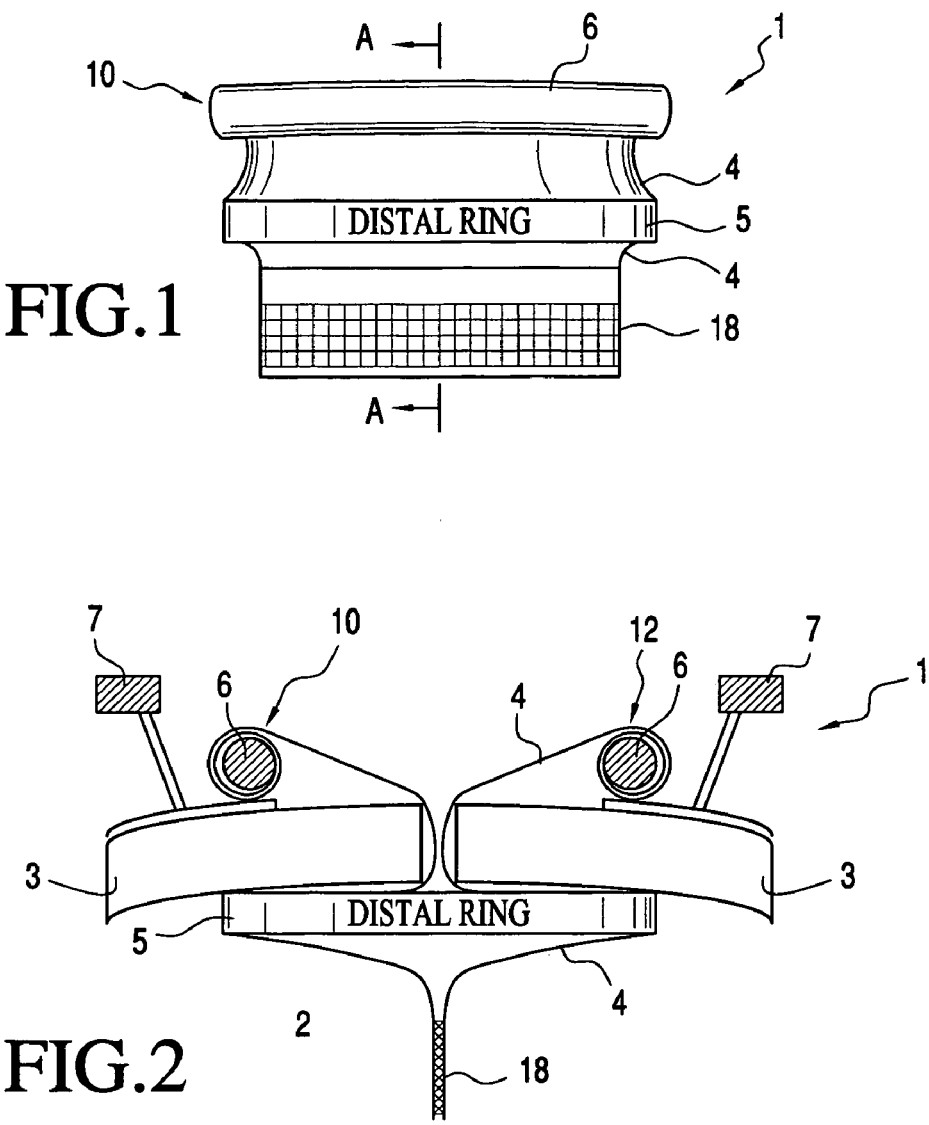
FIG.1
FIG.2
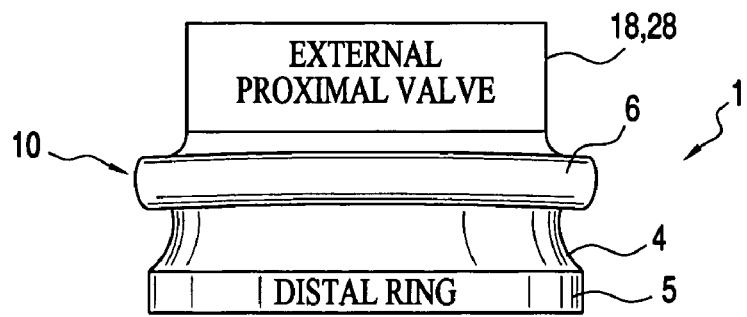
FIG.7

SURGICAL ACCESS DEVICE

BACKGROUND OF THE INVENTION

1. Field of the Invention

The present invention relates to a surgical device for use in minimally invasive surgery of the type using patient pneumoperitoneum and an access port.

2. Description of Related Art

Minimally invasive surgery of this type is carried out having introduced gas into a patient's body cavity through an incision and sealed the incision with an access port. The access port enables laproscopic and hand or instrument assisted surgery to be performed.

A sleeve forming such a port is shown in WO-A-95/07056 entitled "Apparatus for use in surgery". The access port sleeve shown is used to create a controlled pressurized environment within the sleeve while allowing a surgeon's arm to pass through the sleeve. During surgery, gas is pumped into the patient's body cavity where the surgery is to be performed and the sleeve prevents gas escaping while allowing the surgeon to operate using minimally invasive surgery techniques. The application shows a sleeve having a flange at a distal end provided with adhesive for adhering the device to a patient's body or alternatively a mounting ring to surround the incision in a patient's body. While providing a suitable apparatus for performing such surgery the device described suffers from the principle disadvantage that in use, the sleeve protrudes upwardly from the patient and may interfere with the activities of the surgery team. Additionally, the sleeve must be sealed against the surgeon's upper forearm by clamping the device to the arm sufficiently tightly to avoid gas leak around the area of the seal. This presents the surgeon with a problem both in sealing the sleeve and in subsequent mobility.

A further problem associated with the use of sleeves of the kind described is that a phenomenon known as "tenting" may occur. "Tenting" means that when the sleeve is adhered to the patient's skin or to a surgical drape and gas is induced into the patient's abdominal cavity, there is a tendency for the sleeve to fill with gas and to pull away from the patient.

U.S. Pat. No. 5,514,133 discloses an endoscopic surgical apparatus for enabling a surgeon to access directly the surgical site during an endoscopic procedure. This apparatus includes an opening extending longitudinally through the apparatus and prior art is configured and dimensioned to receive a hand therethrough. A first plate engages against the outer surface of the abdominal wall. A second plate is spaced from the first plate and is movable between a first position and a second position wherein the second plate is in close cooperative alignment with the inner surface of the abdominal wall. An adjustment member is mounted to the second plate and actuates movement of the second plate between its first position and its second position. A first sealing member inhibits the flow of gas through said opening and is formed by a pair of overlapping seals. A flexible sleeve extends between the first and second plates and adjusts in length to accommodate various thicknesses of the abdominal wall. The sleeve also creates an access port for the passage of objects through the abdominal wall.

SUMMARY OF THE INVENTION

A surgical device for use in minimally invasive surgery of the type using an inflated body cavity accessible to a surgeon through an access port, defined by the device, surrounding an incision in a patient's body, the device having: body cavity engagement means for insertion into the incision to locate the device in position; fixing means for attaching the device to a patients skin, the fixing means including a proximal ring; a sleeve connectable between the body cavity engagement means and the fixing means wherein the sleeve is adjustable by the positioning of the proximal ring so that the positioning of the proximal ring retracts the sleeve to define an access port and create a seal between the incision and sleeve; and sealing means, at least one of mounted on the sleeve and operating on the sleeve, to prevent substantial leakage of gas from the body cavity on inflation when in an inoperative position and formed to mould about a substantial portion of a surgeon's hand or surgical instrument on insertion in an operating position. Preferably, the body cavity engagement means is provided by a distal ring formed for insertion into the incision.

In one arrangement, the distal ring has an associated self-sealing valve. The fixing means (proximal ring) incorporates adjustment means for modifying the length of the sleeve. This ensures that the fixing means, distal ring and valves are brought into close contact with the abdominal wall ensuring a good seal is maintained and that the device is firmly mounted in position.

BRIEF DESCRIPTION OF THE DRAWINGS

FIG. 1 is a front view of a surgical device in accordance with the invention;

FIG. 2 is a section view in the direction of the arrows A—A of the surgical device of FIG. 1;

FIG. 7 is a front view of another embodiment of the surgical device of the present invention with an external proximal valve instead of an internal distal valve.

DETAILED DESCRIPTION OF THE INVENTION

Figure 3:
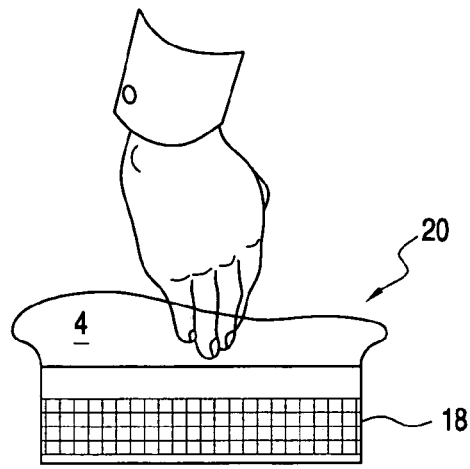
FIG. 3 is a view of the self sealing valve forming part of a surgical device in accordance with the invention in an inoperative position.

Referring to the drawings, and initially to FIGS. 1–2 there is illustrated a surgical device according to the invention, indicated generally by the reference numeral 1. The surgical device 1 is formed for use in minimally invasive surgery of the type using an inflated body cavity indicated generally by the reference numeral 2. The cavity 2 is accessible to a surgeon through an access port, defined by a sleeve 4, passing through an incision in a patient's abdominal wall 3.

In more detail, the device 1 has a body cavity engagement means provided by a distal ring 5 for insertion into the incision to locate the device 1 in position. The distal ring 5 prevents the device from becoming detached from the body inadvertently and has an associated sealing means in the form of a self-sealing valve 18 for sealing the sleeve 4 when not in use. The device 1 is held in position on the patient's skin outside the body by a fixing means 10 provided in this case by a proximal ring 6. The distal ring 5 and proximal ring 6 ensure that the device 1 is securely fixed in position, both rings 5,6 surround the incision and the sleeve 4 passes through the incision connecting the rings 5 and 6. The proximal ring 6 has adjustment means 12 provided by being rotatably mounted on the skin to modify the length of the sleeve 4. This ensures that the fixing means 10 and the distal ring 5 are brought into close contact with the abdominal wall 3, thereby ensuring a good seal is maintained and that the device 1 is firmly mounted in position.

The proximal ring 6 may have a connector ring 7 for receiving additional seals to prevent loss of pressure from the cavity 2. The connector ring 7 may also be used for holding or guiding medical instruments into position over, through or in the incision.

In use, an incision is made in the abdominal wall 3 and the distal ring 5 and associated self-sealing valve 18 is passed through the incision into the cavity 2. The self-sealing valve 18 incorporates elasticized filaments, which are biased toward a closed position or inoperative position (see FIG. 3). The distal ring 5 is moved when in the cavity 2 so that the ring 5 surrounds the incision. The proximal ring 6 can then be rotated, adjusted in height or stretched to take up the surplus material of sleeve 4 on the proximal ring 6. When the distal ring 5 is drawn up to snugly engage the internal abdominal wall 3 surrounding the incision, the proximal ring 6 is attached to the patient's skin to fix the device 1 in position. When in position, the sleeve 4 passing between the portions of the abdominal wall 3 exposed by the incision retracts the incision sides creating a lumen or bore through which an object or hand can be passed. A seal is provided by the self-sealing valve 18.

Figure 4:
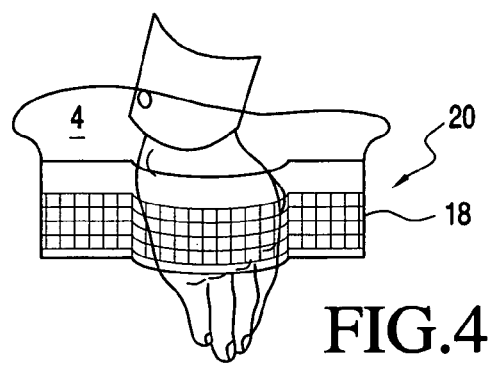
FIG. 4 is a view of portion of the valve shown in FIG. 3 in an operating position.

When a surgeon wishes to gain access to the cavity 2, a hand or instrument is passed down through the sleeve 4. The outward pressure of the retracted sleeve 4 on the abdominal wall ensures that access is not restricted. The self-sealing valve 18 is easily operated by the surgeon to gain access to the cavity 2 and surgery can be performed. As an object is removed, the self-sealing valve 18 closes down sealing the cavity 2. Specifically, when a surgeon passes a hand or instrument between the filaments which run all around the end of the sleeve 4, they are forced out of position into an operating position as shown in FIG. 4. As filaments are used, they accurately mould to the surface of the inserted object preventing loss of gas from the body cavity 2. The memory resident in these filaments returns the valve 18 to the inoperative position once the object is removed to re-seal the sleeve 4.

It will be noted that equivalent methods of dispensing and retracting slack sleeve material following positioning of the device may be used.

Figure 5:
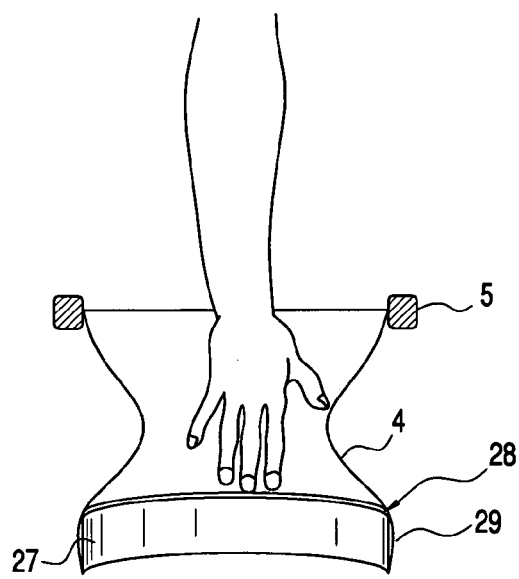
FIG. 5 is a view of a another alternative self sealing valve forming part of a surgical device in accordance with the invention in an inoperative position.
Figure 6:
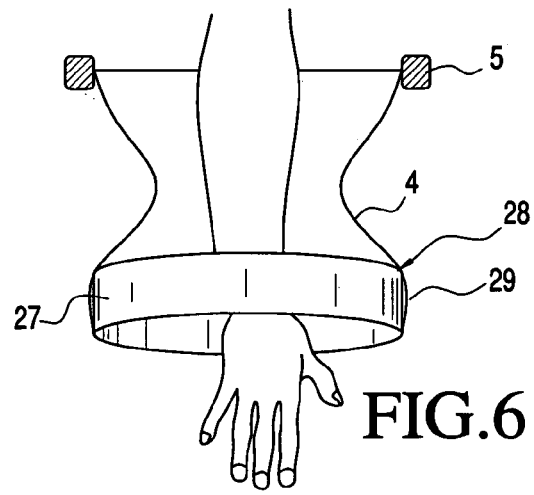
FIG. 6 is a view of portion of the valve shown in FIG. 5 in an operating position.

FIGS. 5 and 6 show an alternative to the self-sealing valve 18 described above in relation to FIGS. 1–4. In this alternative embodiment, a spring valve 28 provides the seal to the sleeve 4. The spring valve 28 is provided by mounting a member 27 within a pocket 29 of the sleeve 4. Tension in the spring valve 28 is provided by forming the member 27 to be longer that the pocket 29. Operation of this valve is identical to that described above.

It will be understood that the operation of these valves is not dependent on the adjustment means described above.

In a still further arrangement, the proximal ring may be adjusted in height by means of inserting compressible foam rings between the proximal ring and the abdominal wall. Alternatively, the sleeve may be made of an elastomer material which when the distal ring is inserted into the incision, stretches the elastomer sheet causing tension between the distal ring and the proximal ring.

It will be understood that the self-sealing valves 18, 28 described herein may be equally used as external proximal valves (FIG. 7) or as internal distal valves.

It will of course be understood that the invention is not limited to the specific details described herein, which are given by way of example only, and that various modifications and alterations are possible within the scope of the invention.

What is claimed is:

1. A surgical device (1) for use in minimally invasive surgery of the type using an inflated body cavity (2) accessible to a surgeon through an access port, defined by the device (1), surrounding an incision in a patient's body, the device (1) having:
   body cavity engagement means (5) for insertion into the incision to locate the device (1) in position;
   fixing means (10) for attaching the device to a patient's skin, the fixing means including a proximal ring (6);
   a sleeve (4) connected between the body cavity engagement means and the fixing means, wherein the sleeve is adjustable by the positioning of the proximal ring so that the positioning of the proximal ring retracts the sleeve to cause the sleeve to apply outward pressure against the patient's body to retract the incision to define an access port and create a seal between the incision and sleeve; and
   sealing means, at least one of mounted on the sleeve and operating on the sleeve, to prevent substantial leakage of gas from the body cavity on inflation when in an inoperative position and formed to mould about a substantial portion of a surgeon's hand or surgical instrument on insertion in an operating position.

2. The surgical device of claim 1 in which the body cavity engagement means (5) is provided by a distal ring (5) formed for insertion into the incision.

3. The surgical device of claim 2, in which the sealing means includes a self-sealing valve mounted on the sleeve.

4. The surgical device of claim 2, in which the fixing means (6) incorporates adjustment means for modifying the length of the sleeve, so as to ensure that the fixing means (6) and the distal ring (5) may be brought into close contact with the abdominal wall ensuring a good seal is maintained and that the device (1) is firmly mounted in position.

5. The surgical device of claim 1, further including a connector ring (7) mounted adjacent said proximal ring.

6. The surgical device of claim 1, in which the sleeve is made of an elastomer material, whereby insertion of the distal ring into an incision stretches the elastomer material causing tension between the distal ring and proximal ring.

7. The surgical device of claim 1, wherein said sealing means is an external proximal valve mounted adjacent to said proximal ring.

8. The surgical device of claim 1, wherein said sealing means is an internal distal valve.

9. The surgical device of claim 1, wherein said sealing means is a self-sealing valve formed of elasticized filaments.

10. The surgical device of claim 1, wherein said sealing means is a self-sealing spring valve including a tensioned member mounted on the sleeve.

11. A surgical device for use in minimally invasive surgery of the type using an inflated cavity accessible to a surgeon through an access port, defined by the device, surrounding an incision in a patient's body, the device comprising:
   body cavity engagement means for insertion into the incision to locate the device in position, said body cavity engagement means including a distal ring;
   fixing means for attaching the device to a patient's skin, said fixing means including a proximal ring;

a sleeve connected between the body cavity engagement means and the fixing means, said sleeve having an adjustable length that shortens to cause said sleeve to apply outward pressure against the patient's body sufficient to retract the incision to define the access port; and one of an external proximal sealing valve mounted adjacent to said proximal ring and an internal distal sealing valve mounted adjacent to said distal ring, to prevent substantial leakage of gas from the body cavity on inflation when in an operative position and formed to mold about a substantial portion of a surgeon's hand or surgical instrument on insertion in an operating position.

12. The surgical device of claim 11, wherein said one of an external proximal sealing valve mounted adjacent to said proximal ring and an internal distal sealing valve mounted adjacent to said distal ring is a self-sealing valve formed of elasticized filaments.

13. The surgical device of claim 11, wherein said one of an external proximal sealing valve mounted adjacent to said proximal ring and an internal distal sealing valve mounted adjacent to said distal ring is a self-sealing spring valve including a tensioned member mounted on the sleeve.

14. A surgical device for use in minimally invasive surgery of the type using an inflated cavity accessible to a surgeon through an access port, defined by the device, surrounding an incision in a patient's body, the device comprising:

body cavity engagement means for insertion into the incision to locate the device in position, said body cavity engagement means including a distal ring;

fixing means for attaching the device to a patient's skin, said fixing means including a proximal ring;

a sleeve connected between the body cavity engagement means and the fixing means, said sleeve having a length;

wherein said proximal ring includes an adjustment means for adjusting the length of said sleeve to cause said sleeve to apply outward pressure against the patient's body sufficient to retract sides of the incision; and one of an external proximal sealing valve mounted adjacent to said proximal ring and an internal distal sealing valve mounted adjacent to said distal ring, to prevent substantial leakage of gas from the body cavity on inflation when in an operative position and formed to mold about a substantial portion of a surgeon's hand or surgical instrument on insertion in an operating position.

15. The surgical device of claim 14, wherein said one of an external proximal sealing valve mounted adjacent to said proximal ring and an internal distal sealing valve mounted adjacent to said distal ring is a self-sealing valve formed of elasticized filaments.

16. The surgical device of claim 14, wherein said one of an external proximal sealing valve mounted adjacent to said proximal ring and an internal distal sealing valve mounted adjacent to said distal ring is a self-sealing spring valve including a tensioned member mounted on the sleeve.

* * * * *